United States Patent [19]

Rothfuss

[11] 4,014,492
[45] Mar. 29, 1977

[54] SURGICAL STAPLE
[75] Inventor: Robert G. Rothfuss, Bellevue, Ky.
[73] Assignee: Senco Products, Inc., Cincinnati, Ohio
[22] Filed: June 11, 1975
[21] Appl. No.: 585,804
[52] U.S. Cl. .............................. 227/19; 227/132; 128/337; 85/49
[51] Int. Cl.$^2$ ............... B25C 5/10; B25C 5/16; A61B 17/10
[58] Field of Search ............... 128/334, 335, 337; 85/49; 227/19, 132

[56] References Cited
UNITED STATES PATENTS

| | | | |
|---|---|---|---|
| 1,728,316 | 9/1929 | Wachenfeldt | 128/334 R |
| 1,868,100 | 7/1932 | Goodstein | 85/49 |
| 1,910,688 | 5/1933 | Goodstein | 85/49 |
| 1,939,631 | 12/1933 | Randall | 85/49 X |
| 1,945,377 | 1/1934 | Posnack | 227/132 X |
| 2,201,610 | 5/1940 | Dawson | 128/337 |
| 2,277,931 | 3/1942 | Moe | 85/49 |
| 2,684,070 | 7/1954 | Kelsey | 128/337 |
| 3,643,851 | 2/1972 | Green et al. | 227/19 |

Primary Examiner—Dalton L. Truluck
Attorney, Agent, or Firm—Melville, Strasser, Foster & Hoffman

[57] ABSTRACT

A surgical staple for use in joining the skin or fascia of a patient. The staple is adapted to be formed about an anvil during emplacement. The staple has points formed by diagonal cuts across the ends, and its configuration prior to emplacement is such, that the diagonal cuts are perpendicular to the upper surface of the anvil and the skin or fascia, whereby the staple penetrates the skin or fascia without the tendency to slide therealong. The configuration is such that at initial contact of the staple points with the skin or fascia, the points lie substantially in the plane of the forming corners of the anvil, thereby affording greater skin gathering during emplacement. The configuration disclosed facilitates stacking of the staples for use in a cartridge, and provides for an improvement in the space factor within the cartridge over staples of conventional shape.

8 Claims, 8 Drawing Figures

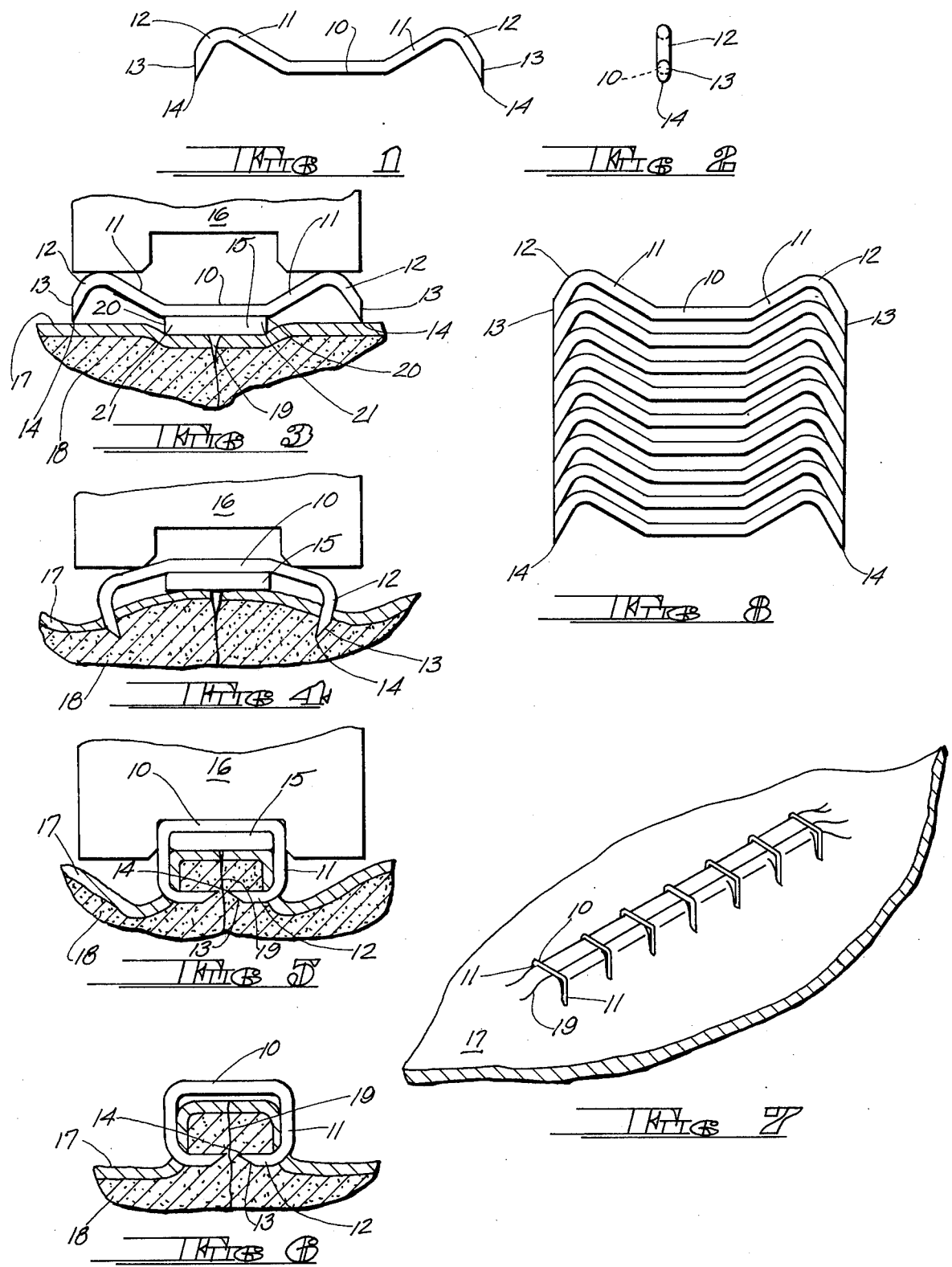

SURGICAL STAPLE

BRIEF SUMMARY OF THE INVENTION

In recent years, surgeons have come more and more to the use of staples for closing wounds or incisions in the skin and fascia instead of conventional thread sutures in surgical operations. One of the main reasons for this trend is that the conventional suture which involves insertion of a thread by means of a curved needle and then tying the ends of the thread is quite time-consuming. There are various operations in which a large number of sutures must be used. Thus, for example, in heart surgery where coronary by-pass procedures are performed, the by-passes are usually made from the saphenous vein in the leg. It is common to perform as many as six incisions in the leg from the ankle to the groin in dissecting out the saphenous vein from which the by-passes are to be made. The several incisions involved may vary from perhaps two inches in length to six or seven inches in length. With conventional thread sutures the closing of such wounds would take perhaps an hour to an hour and a half, whereas with surgical staples as many as fifty staples may be emplaced in a matter of ten to twenty minutes. This saving of time is of great importance in that it not only saves the surgeon's time but it reduces fatigue on the part of the surgeon and it substantially reduces the length of time the patient must be maintained under anaesthesia. It is generally recognized that the shorter the time the patient is under anaesthesia, the more rapid is his recovery and the less trauma is involved.

Presently available surgical staples leave much to be desired by way of design and function. They are generally shaped like conventional staples that are used in wood or paper except that they are generally wider and have short legs. They are formed about an anvil into a box configuration. There has been observed a tendency for the points of such staples to slide across the skin along their cut surfaces before penetrating and in doing so the staples could tend to separate the wound before the points actually penetrate the skin. In the conventional staple the points are relatively close to the forming corners of the anvil about which they are formed when the staple first contacts the skin and again when the staple contacts the anvil. Thus, they do not always obtain a secure and effective wound closing since in order to accomplish this the staple must gather skin and tissue sufficiently to close the wound and to cause the edges of the wound to be brought into approximation.

Staples of the prior art and of the present invention are provided in a cartridge and the configuration of the staple disclosed herein substantially improves the space factor and makes it possible to stack more staples in a given space in a cartridge than is possible with staples of conventional form.

Very briefly, a staple according to the present invention prior to emplacement is configured with a central portion, a straight portion extending upwardly and outwardly from each end of the central portion at an obtuse angle, and a relatively short straight portion extending downwardly and outwardly from each of said upwardly and outwardly extending portions. The downwardly and outwardly extending portions have vertical cuts to produce sharp points at the ends of the downwardly and outwardly extending portions. The vertical cuts will be normal to the surface of the skin at the time of initial contact. The disposition of the points with respect to the forming anvil about which the staple is formed is of considerable importance and the configuration to be described hereinafter produces an eversion of the wound which insures proper approximation and better and more rapid healing.

BRIEF DESCRIPTION OF THE SEVERAL VIEWS OF THE DRAWING

FIG. 1 is an elevational view of a surgical staple according to the present invention.

FIG. 2 is an end elevational view thereof.

FIG. 3 is a view showing a staple according to the present invention in its relation to the forming anvil, the forming die and the wound which is to be closed.

FIG. 4 is a view similar to FIG. 3 showing the staple in the process of being formed.

FIG. 5 is a similar view showing the staple completely formed closing the wound.

FIG. 6 is a view similar to FIG. 5 showing the wound after the tool and anvil have been removed.

FIG. 7 is a perspective view of a wound properly closed by a plurality of staples according to the invention.

FIG. 8 is an elevational view showing how a plurality of staples may be nested together or stacked for placement in a cartridge.

DETAILED DESCRIPTION

As seen in FIG. 1 the staple has a central portion 10 with upwardly and outwardly extending portions 11 which extend at an obtuse angle to the portion 10. From the ends of the portions 11 there extend downwardly and outwardly the portions 12 which are shown as disposed at substantially right angles to the portions 11. The ends of the portions 12 are cut vertically as at 13 to provide the sharp points 14.

In FIGS. 3 and 6 inclusive, the emplacement of a staple to close the wound is shown progressively. In these Figures, the forming anvil about which the staple is formed is indicated at 15 and the forming die is indicated at 16. The skin of the patient is indicated at 17 and the underlying tissues at 18. The incision which is being closed is indicated at 19.

FIG. 3 serves to illustrate the disposition of the points 14 with respect to the anvil 15. It will be noted that the upper corners of the anvil are curved as indicated at 20 and the radii of curvature of the curves 20 are indicated by the points 21. It will be observed that the points 14 of the staple are approximately in the plane of the centers of curvature 21 of the curves 20. This configuration insures that the first bending effort of the die 6 against the portions 11 produces a penetration of the skin by the points 14 rather than a sliding of the points along the skin and insures greater skin gathering than hitherto obtained.

In FIG. 4 the points 14 have penetrated the skin 17 and underlying tissues 18 and it will be seen that the portions 11 and 12 of the staple are being bent in a curve about the points 21.

In FIG. 5 the staple has been completely formed and in FIG. 6 the tool and anvil have been withdrawn, i.e. the formed staple has been ejected from the tool and anvil. It will be seen that the incision is nicely closed and is properly everted to produce the desired approximation and to enhance the healing process.

FIG. 7 shows clearly how the closed wound looks with the wound properly everted.

By virtue of the configuration described above, a plurality of staples may be stacked together for insertion into a cartridge or magazine as shown in FIG. 8. The point forming cuts 14 will form parallel straight lines and only the portions 12 of the staples will be in contact with each other. This not only improves the space factor and makes it possible to stack a greater number of staples in a given space than with conventional staples, but also makes it easy to separate the staples for driving.

It will be clear that modifications may be made without departing from the spirit of the invention. Thus, for example, the drawing, in FIG. 2, shows the staple as being circular in cross section; but square or rectangular cross sections may be found desirable for certain purposes. Similarly, the staples have been shown with a straight central portion, and with the portions 11 and 12 at right angles to each other. While these configurations are preferred, they are not essential to the usefulness of the staples. Therefore no limitations which are not specifically set forth in the claims are intended and no such limitations should be implied.

The embodiments of the invention in which an exclusive property or privilege is claimed are defined as follows:

1. In combination with a stapling tool having a forming anvil and a cooperating forming die, a surgical staple for joining the severed skin or fascia of a patient, said staple, prior to emplacement, being configured with a straight central portion of a length approximately equal to the width of said forming anvil, a straight portion extending upwardly and outwardly from each end of said central portion at an obtuse angle, and a relatively short straight portion extending downwardly and outwardly from the uppermost end of each of said upwardly and outwardly extending portions, said downwardly and outwardly extending portions terminating in vertical outer surfaces producing sharp points at the lowermost ends of said downwardly and outwardly extending portions, the upper corners of said forming anvil, about which said staple is formed by said die during emplacement of the staple, having a small radius of curvature, the points of said staple prior to emplacement, lying approximately in a horizontal plane passing through the centers of curvature of said small radii, said staple, when emplaced by said tool, having a box-like configuration, with the skin or fascia being joined thereby, everted within said box-like configuration.

2. The structure claimed in claim 1 wherein said relatively short straight portions extend downwardly and outwardly at right angles from said upwardly and outwardly extending portions.

3. A surgical staple for joining the severed skin or fascia of a patient, said staple, prior to emplacement, being configured with a straight central portion, a straight portion extending upwardly and outwardly from each end of said central portion at an obtuse angle, and a relatively short straight portion extending downwardly and outwardly from the uppermost end of each of said upwardly and outwardly extending portions, said downwardly and outwardly extending portions terminating in outer vertical surfaces producing sharp points at the lowermost ends of said downwardly and outwardly extending portions 4. The structure claimed in claim 1 wherein said sharp points of said staple lie approximately in a horizontal plane spaced beneath said central portion by a distance not greater than the thickness of said straight central portion.

5. The structure claimed in claim 1 wherein said relatively short straight portions extend downwardly and outwardly at right angles from said upwardly and outwardly extending portions.

6. A stick of staples constituted of a plurality of staples according to claim 1 nested together with the inner surfaces of the relatively short straight portions of one staple abutting the outer surfaces of the relatively short straight portions of an adjacent staple, and with the vertical surfaces producing the sharp points forming parallel straight lines.

7. The structure of claim 6 wherein only said relatively short straight portions of adjacent staples are in contact with each other.

8. A surgical staple for joining the severed skin or fascia of a patient, said staple, after emplacement in the skin or fascia of the patient, having a box-like configuration, with the skin or fascia being joined thereby everted within said box-like configuration, with the top and sides of said box-like configuration outside of the skin or fascia being joined thereby, and with the bottom of said box-like configuration extending into the skin or fascia being joined thereby, and said staple, prior to emplacement, being configured with a straight central portion substantially corresponding to the top of said box-like configuration, a straight portion extending upwardly and outwardly from each end of said central portion at an obtuse angle substantially corresponding to the sides of said box-like configuration, and a relatively short straight portion extending downwardly and outwardly from the uppermost end of each of said upwardly and outwardly extending portions, each of said downwardly and outwardly extending portions substantially corresponding to one half of the bottom of said box-like configuration, said downwardly and outwardly extending portions terminating in outer vertical surfaces producing sharp points at the lowermost ends of said downwardly and outwardly extending portions.

* * * * *